US010070952B2

(12) United States Patent
Franssen et al.

(10) Patent No.: US 10,070,952 B2
(45) Date of Patent: Sep. 11, 2018

(54) APPARATUS, SYSTEM, AND METHOD FOR PROVIDING AN IMPLANTABLE RING FOR ALTERING A SHAPE OF THE CORNEA

(71) Applicant: AMO Groningen B.V., Groningen (NL)

(72) Inventors: Luuk Franssen, Groningen (NL); Hendrik A. Weeber, Groningen (NL); Marrie H. Van Der Mooren, Groningen (NL); Carmen Canovas Vidal, Groningen (NL); Kaccie Y. Li, Engelbert (NL); Sieger Meijer, Zuidlaren (NL); Richard Hartman, Haogezand (NL)

(73) Assignee: AMO Groningen B.V., Groningen (NL)

( * ) Notice: Subject to any disclaimer, the term of this patent is extended or adjusted under 35 U.S.C. 154(b) by 0 days.

(21) Appl. No.: 15/419,879

(22) Filed: Jan. 30, 2017

(65) Prior Publication Data
US 2017/0135808 A1    May 18, 2017

Related U.S. Application Data

(62) Division of application No. 14/196,826, filed on Mar. 4, 2014, now Pat. No. 9,554,891.
(Continued)

(51) Int. Cl.
*A61F 2/14*    (2006.01)
*A61F 2/48*    (2006.01)

(52) U.S. Cl.
CPC .............. *A61F 2/142* (2013.01); *A61F 2/147* (2013.01); *A61F 2002/48* (2013.01);
(Continued)

(58) Field of Classification Search
CPC ........ A61F 2/147; A61F 2/1694; A61F 9/013; A61F 9/0017; A61L 27/16
See application file for complete search history.

(56) References Cited

U.S. PATENT DOCUMENTS

| 4,134,161 A | 1/1979 | Bayers |
| 4,136,466 A | 1/1979 | Wrue |

(Continued)

FOREIGN PATENT DOCUMENTS

| DE | 102006036800 A1 | 2/2008 |
| EP | 94158 A1 | 11/1983 |

(Continued)

OTHER PUBLICATIONS

Ayaki M. et al., "Histopathologic Study of After-Cataract in the Pseudophakic Rabbit Eye Using in-the-Bag Fixation (II)," Nippon Ganka Gakkai Zasshi, 1990, vol. 94 (6), pp. 559-565 (Abstract Only).
(Continued)

*Primary Examiner* — David H Willse
*Assistant Examiner* — Tiffany Shipmon
(74) *Attorney, Agent, or Firm* — Johnson & Johnson Surgical Vision, Inc.

(57) ABSTRACT

An apparatus, system and method for constricting a cornea of a human eye are disclosed. A control device external to the subject eye, such as an induction generator, may be configured to create a stimulus, such as a magnetic field, for an implanted ring that, when stimulated, may change the curvature, and thus the dioptric power, of the eye, thereby approximating natural accommodation.

7 Claims, 7 Drawing Sheets

Related U.S. Application Data

(60) Provisional application No. 61/784,226, filed on Mar. 14, 2013.

(52) U.S. Cl.
CPC ... *A61F 2210/009* (2013.01); *A61F 2220/005* (2013.01); *A61F 2220/0025* (2013.01); *A61F 2220/0075* (2013.01); *A61F 2250/001* (2013.01)

(56) References Cited

U.S. PATENT DOCUMENTS

| | | | |
|---|---|---|---|
| 4,219,721 A | 8/1980 | Kamen et al. | |
| 4,403,354 A | 9/1983 | Rainin | |
| 4,435,855 A | 3/1984 | Pannu | |
| 4,443,441 A | 4/1984 | Galin | |
| 4,463,457 A | 8/1984 | Kelman | |
| 4,559,942 A | 12/1985 | Eisenberg | |
| 4,575,373 A | 3/1986 | Johnson | |
| 4,585,456 A | 4/1986 | Blackmore | |
| 4,617,023 A | 10/1986 | Peyman | |
| 4,642,113 A | 2/1987 | Dubroff | |
| 4,661,109 A | 4/1987 | White | |
| 4,662,882 A | 5/1987 | Hoffer | |
| 4,666,445 A | 5/1987 | Tillay | |
| 4,676,793 A | 6/1987 | Bechert, II | |
| 4,681,585 A | 7/1987 | Sayano et al. | |
| 4,685,921 A | 8/1987 | Peyman | |
| 4,685,922 A | 8/1987 | Peyman | |
| 4,687,485 A | 8/1987 | Lim et al. | |
| 4,704,016 A | 11/1987 | De Carle | |
| 4,764,930 A | 8/1988 | Bille et al. | |
| 4,781,718 A | 11/1988 | Lindstrom | |
| 4,834,753 A | 5/1989 | Sulc et al. | |
| 4,872,876 A | 10/1989 | Smith | |
| 4,946,470 A | 8/1990 | Sulc et al. | |
| 5,108,429 A | 4/1992 | Wiley | |
| 5,147,395 A | 9/1992 | Willis | |
| 5,217,491 A | 6/1993 | Vanderbilt | |
| 5,225,858 A | 7/1993 | Portney | |
| 5,259,813 A | 11/1993 | Abthoff et al. | |
| 5,269,813 A | 12/1993 | Yoshida et al. | |
| 5,288,293 A | 2/1994 | O'Donnell | |
| 5,571,177 A | 11/1996 | Deacon et al. | |
| 5,713,892 A | 2/1998 | Shimmick | |
| 5,728,156 A | 3/1998 | Gupta et al. | |
| 5,984,962 A | 11/1999 | Anello et al. | |
| 5,993,438 A | 11/1999 | Juhasz et al. | |
| 6,210,005 B1 | 4/2001 | Portney | |
| 6,511,508 B1 | 1/2003 | Shahinpoor et al. | |
| 6,887,083 B2 | 5/2005 | Umeyama et al. | |
| 6,923,955 B2 | 8/2005 | Till et al. | |
| 6,976,997 B2* | 12/2005 | Noolandi | A61F 2/142 623/5.14 |
| 7,044,945 B2 | 5/2006 | Sand | |
| 2001/0010019 A1 | 7/2001 | Schachar | |
| 2002/0103478 A1 | 8/2002 | Gwon et al. | |
| 2003/0028248 A1 | 2/2003 | Shahinpoor et al. | |
| 2003/0139808 A1* | 7/2003 | Shahinpoor | A61F 2/147 623/4.1 |
| 2004/0082993 A1 | 4/2004 | Woods | |
| 2004/0111153 A1 | 6/2004 | Woods et al. | |
| 2004/0153150 A1 | 8/2004 | Ghazizadeh et al. | |
| 2004/0199149 A1 | 10/2004 | Myers et al. | |
| 2004/0243111 A1 | 12/2004 | Bendett et al. | |
| 2006/0253196 A1 | 11/2006 | Woods | |
| 2006/0265058 A1 | 11/2006 | Silvestrini | |
| 2007/0185475 A1 | 8/2007 | Frey et al. | |
| 2008/0140192 A1 | 6/2008 | Humayun et al. | |
| 2008/0161913 A1 | 7/2008 | Brady et al. | |
| 2008/0161914 A1 | 7/2008 | Brady et al. | |
| 2010/0292678 A1 | 11/2010 | Frey et al. | |

FOREIGN PATENT DOCUMENTS

| | | |
|---|---|---|
| EP | 0278724 A2 | 8/1988 |
| EP | 336318 A2 | 10/1989 |
| EP | 478929 A1 | 4/1992 |
| SU | 1424828 A1 | 9/1988 |
| WO | 8701931 A1 | 4/1987 |
| WO | 9007914 A1 | 7/1990 |
| WO | 9749354 A1 | 12/1997 |
| WO | 0182815 A1 | 11/2001 |
| WO | 02071976 A2 | 9/2002 |
| WO | 03057081 A2 | 7/2003 |
| WO | 2004039295 A1 | 5/2004 |
| WO | 2004039395 A1 | 5/2004 |
| WO | 04082542 A2 | 9/2004 |
| WO | 2007084602 A2 | 7/2007 |
| WO | 2010059847 A1 | 5/2010 |

OTHER PUBLICATIONS

Ayaki M., et al., "Histopathologic Study of After-Cataract in the Pseudophakic Rabbit Eye Using Out-of-the-Bag Fixation," Nippon Ganka Gakkai Zasshi, 1990, vol. 94 (6), pp. 553-558 (Abstract Only).

Biedner B., et al., "Subconjunctival Dislocation of Intraocular Lens Implant," American Journal of Opthalmology, 1977, vol. 84 (2), pp. 265-266.

Bloom S.M., et al., "Scleral Fixation Suture for Dislocated Posterior Chamber Intraocular Lens," Ophthalmic Surgery, 1990, vol. 21 (12), pp. 851-854.

Bowman C.B., et al., "Noninvasive Repositioning of a Posterior Chamber Intraocular Lens Following Pupillary Capture," Journal of Cataract and Refractive Surgery, 1991, vol. 17 (6), pp. 843-847.

Chan B.P., et al., "Effects of Photochemical Crosslinking on the Microstructure of Collagen and a Feasibility Study on controlled Protein Release," Acta Biomaterialia, 2008, vol. 4 (6), pp. 1627-1636.

Chan C.K., "An Improved Technique for Management of Dislocated Posterior Chamber Implants," Ophthalmology, 1992, vol. 99 (1), pp. 51-57.

Corcoran M.F., "Spontaneous Repositioning of a Dislocated Medallion Intraocular Lens," Journal of the American Intra-Ocular Implant Society, 1985, vol. 11 (6), pp. 598-599.

Flynn H.W., et al., "Management of Subluxated and Posteriorly Dislocated Intraocular Lenses Using Pars Plana Vitrectomy Instrumentation," Journal of Cataract and Refractive Surgery, 1990, vol. 16 (1), pp. 51-56.

Flynn H.W., "Pars Plana Vitrectomy in the Management of Subluxed and Posteriorly Dislocated Intraocular Lenses," Graefe's Archive for Clinical and Experimental Ophthalmology, 1987, vol. 225 (3), pp. 169-172.

Friedberg M.A., et al., "A New Technique for Repositioning and Fixating a Dislocated Intraocular Lens," Archives of Ophthalmology, 1992, vol. 110 (3), pp. 413-415.

Glasser A., "Accommodation" in: Encyclopedia of Eye, vol. 1, Dartt D.A., ed., Oxford Academic Press, 2010, pp. 8-17.

Glasser A., et al., "Accommodation and Presbyopia" in: Adler's Physiology of the Eye, Clinical Application, 10th Edition and 7th Chapter, Kaufman P.L., et al., Eds., Mosby, 2002, pp. 195-233.

Glasser A., "Physiology of Accommodation and Presbyopia" in: Surgery for Hyperopia, Chapter. 2, Sher N.A., Ed., SLACK, Inc., 2004, pp. 11-21.

Glasser A., "The Helmholtz Mechanism of Accommodation" in: Hyperopia and Presbyopia, Chapter 3, Tsubota K., et al., eds., Marcel Dekker, Inc., 2003, pp. 27-47.

Henderson B.A., et al., "Stepwise Approach to Establishing an Ophthalmology Wet Laboratory," Journal of Cataract & Refractive Surgery, 2009, vol. 35 (6), pp. 1121-1128.

Hovanesian J.A., et al., "Cataract Wound Closure with a Polymerizing Liquid Hydrogel Ocular Bandage," Journal of Cataract & Refractive Surgery, 2009, vol. 35 (5), pp. 912-917.

(56) References Cited

OTHER PUBLICATIONS

Hovanesian J.A., et al., "Watertight Cataract Incision Closure Using Fibrin Tissue Adhesive," Journal of Cataract & Refractive Surgery, 2007, vol. 33 (8), pp. 1461-1463.
International Search Report and Written Opinion for Application No. PCT/US2012/028090, dated Sep. 25, 2012, 19 Pages.
International Search Report and Written Opinion for Application No. PCT/US2012/028095, dated Jun. 19, 2012, 11 pages.
International Search Report and Written Opinion, dated Jan. 14, 2010, and International Preliminary Report on Patentability, dated Mar. 29, 2011, for Application No. PCT/US2009/058321, 11 pages.
International Search Report for Application No. PCT/US2010/050752, dated Mar. 22, 2011, 5 pages.
International Search Report for Application No. PCT/US94/06403, dated Sep. 20, 1994, 4 pages.
Lyons C.J., et al., "Report of a Repositioned Posteriorly Dislocated Intraocular Lens via Pars Plicata Sclerotomy," Journal of Cataract Refractive Surgery, 1990, vol. 16 (4), pp. 509-511.
Menabeuoni L., et al., "Laser-Assisted Corneal Welding in Cataract Surgery: Retrospective Study," Journal of Cataract and Refractive Surgery, 2007, vol. 33 (9), pp. 1608-1612.
Moretsky S.L., "Suture Fixation Technique for Subluxated Posterior Chamber IOL through Stab Wound Incision," Journal of the American Intra-Ocular Implant Society, 1984, vol. 10 (4), pp. 477-480.
Nabors G., et al., "Ciliary Sulcus Suturing of a Posterior Chamber Intraocular Lens," Ophthalmic Surgery, 1990, vol. 21 (4), pp. 263-265.
Neumann A.C., et al., "Complications Associated with STAAR Silicone Implants," Journal of Cataract and Refractive Surgery, 1987, vol. 13 (6), pp. 653-656.
Nevyas H.J., et al., "A YAG Laser Technique to Facilitate Removal of Posterior Chamber Intraocular Lenses from the Capsular Bag," Journal of Cataract and Refractive Surgery, 1987, vol. 13 (2), pp. 201-204.
Pandey S.K., et al., "Creating Cataracts of Varying Hardness to Practice Extracapsular Cataract Extraction and Phacoemulsification," Journal of Cataract & Refractive Surgery, 2000, vol. 26 (3), pp. 322-329.
Pandey S.K., et al., "Induction of Cataracts of Varying Degrees of Hardness in Human Eyes Obtained Postmortem for Cataract Surgeon Training," American Journal of Ophthalmology, 2000, vol. 129 (4), pp. 557-558.
Partial International Search Report for Application No. PCT/US2012/028090, dated May 29, 2012, 6 pages.
Pau H., "Cortical and Subcapsular Cataracts: Significance of Physical Forces," Ophthalmologica, 2006, vol. 220 (1), pp. 1-5.
Poley B.J., et al., "A Closed Technique for Repositioning Dislocated Iris Plane Lenses," Journal of the American Intra-Ocular Implant Society, 1979, vol. 5 (4), pp. 316-320.
Praeger D.L., "Praeger Micro Irrigating Hook Intraocular Lens Implantation," Ophthalmic Surgery, 1979, vol. 10 (7), pp. 30-32.
Ripken T., et al., "Fs-Laser Induced Elasticity Changes to Improve Presbyopic Lens Accommodation," Graefe's Archive for Clinical and Experimental Ophthalmology, 2008, vol. 246 (6), pp. 897-906.
Shentu X., et al., "Combined Microwave Energy and Fixative Agent for Cataract Induction in Pig Eyes," Journal of Cataract & Refractive Surgery, 2009, vol. 35 (7), pp. 1150-1155.
Smiddy W.E., "Dislocated Posterior Chamber Intraocular Lens: A New Technique of Management," Archives of Ophthalmology, 1989, vol. 107 (11), pp. 1678-1680.
Smiddy W.E., et al., "Management of Dislocated Posterior Chamber Intraocular Lenses," Ophthalmology, 1991, vol. 98 (6), pp. 889-894.
Stark W.J., et al., "Management of Posteriorally Dislocated Intraocular Lenses," Ophthalmic Surgery, 1980, vol. 11 (8), pp. 495-497.
Sternberg P., et al., "Treatment of Dislocated Posterior Chamber Intraocular Lenses," Archives of Ophthalmology, 1986, vol. 104 (9), pp. 1391-1393.
Sugiura T., et al., "Creating Cataract in a Pig Eye," Journal of Cataract & Refractive Surgery, 1999, vol. 25 (5), pp. 615-621.
Tseng Y., et al., "How Actin Crosslinking and Bundling Proteins Cooperate to Generate an Enhanced Cell Mechanical Response," Biochemical and Biophysical Research Communications, 2005, vol. 334 (1), pp. 183-192.
Wand M., et al., "Thymoxamine Hydrochloride:An Alpha-adrenergic Blocker," Survey of Ophthalmology, 1980, vol. 25 (2), pp. 75-84.
Weeber H.A., et al., "The Role of the Capsular Bag in Accommodation" in: Current Aspects of Human Accommodation II, Guthoff R., eds., Heidelberg, Kaden Verlag, 2003, pp. 119-126.

* cited by examiner

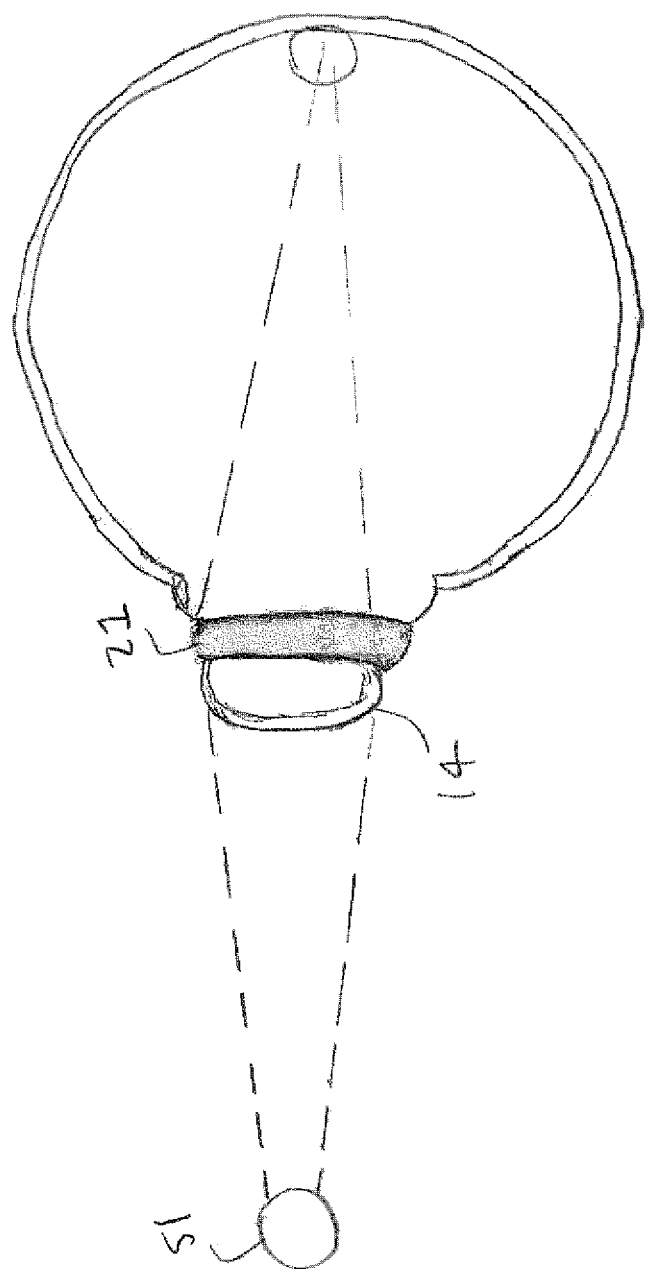

APPARATUS, SYSTEM, AND METHOD FOR PROVIDING AN IMPLANTABLE RING FOR ALTERING A SHAPE OF THE CORNEA

CROSS-REFERENCED TO RELATED APPLICATIONS

This application is a divisional of and claims priority to U.S. patent application Ser. No. 14/196,826, filed Mar. 4, 2014, which claims priority to U.S. Provisional Application No. 61/784,226 filed on Mar. 14, 2013, the entire contents of which are incorporated herein by reference.

FIELD OF THE INVENTION

The instant disclosure relates to implantable devices, and, more particularly, to an apparatus, system, and method for providing an implantable ring for altering a shape of the cornea.

BACKGROUND OF THE INVENTION

Surgery on the human eye has become commonplace in recent years. Many patients pursue eye surgery as an elective procedure in order to avoid the use of contacts or glasses, while other patients find it necessary to pursue surgery to correct an adverse condition in the eye. Such adverse conditions may include, for example, cataracts. A cataract increases the opacity of the natural lens of the eye, causing impaired vision or blindness. Correction may be achieved by surgically removing a cloudy or diseased lens in the patient's eye and replacing it with an artificial lens, known as an intraocular lens (IOL).

The anatomy and physiology of the human eye is well understood. Generally speaking, the structure of the human eye includes an outer layer formed of two parts, namely the cornea and the sclera. The middle layer of the eye includes the iris, the choroid, and the ciliary body. The inner layer of the eye includes the retina. The eye also includes, physically associated with the middle layer, a crystalline lens that is contained within an elastic capsule, referred to herein as the lens capsule, or capsular bag.

Image formation in the eye occurs by entry of image-forming light to the eye through the cornea, and refraction by the cornea and the crystalline lens to focus the image-forming light on the retina. The retina provides the light sensitive tissue of the eye.

Functionally, the cornea has a greater, and generally constant, optical power in comparison to the crystalline lens. The power of the crystalline lens, while smaller than that of the cornea, may be changed when the eye needs to focus at different distances. This change, or "accommodation," is achieved by changing the shape of the crystalline lens. Accommodation, as used herein, includes the making of a change in the focus of the eye for different distances. For example, in order to change the shape of the crystalline lens for accommodation, the ciliary muscles may relax to cause ligaments (zonules) that support the crystalline lens to relax, thereby allowing the crystalline lens to become more rounded.

The iris operates to change the aperture size of the eye. More specifically, the diameter of the incoming light beam is controlled by the iris, which forms the aperture stop of the eye, and the ciliary muscles may contract, as referenced above, to provide accommodation in conjunction with any needed change in the size of the aperture provided by the iris. The opening, or aperture, in the iris is called the pupil.

Correction of defects or degradation in the aspects of the eye may occur surgically, as mentioned above, or non-surgically. In a simple example, it is common to wear glasses or contact lenses to improve vision by correcting myopic (near-sighted), hyperopic (far-sighted) and astigmatic eyesight. Rather than relying on glasses or contacts, elective laser refractive surgery, or other eye surgery, may serve to improve the refractive state of the eye, and may thereby decrease or eliminate dependence on glasses or contact lenses. Additional surgeries may include various methods of surgical remodeling of the cornea, or cataract surgery, for example.

Presbyopia, referenced above, is an adverse condition in which the eye loses the ability to accommodate. Presbyopia is one of the adverse conditions of the eye for which the aforementioned surgical and non-surgical treatments have proven relatively successful. However, many of the aforementioned treatments, such as those in which eye-glasses and contact lenses are employed, provide only temporary solutions for adverse eye conditions and particularly for adverse eye conditions such as presbyopia that cause a loss of capability for accommodation.

In other, non-ocular medical fields, in order to provide a more long-lasting solution for biologic adversities, externally controllable treatments, such as ionic polymer-metal composites, have recently been explored as possible treatment options. For example, these composites have been explored for use with artificial limbs and/or limbs that lack sufficient muscular and/or nervous system control or strength.

Accordingly, it may be advantageous to employ the use of externally controllable treatments, such as ionic polymer-metal composites, to the eye, and, in particular, to the cornea. Such a solution may provide another, potentially more viable and long term solution to the correction of adverse eye conditions, such as presbyopia, by allowing for alteration of a shape of the cornea.

SUMMARY OF THE INVENTION

An apparatus, system and method for constricting a cornea of a human eye are disclosed. A control device external to the subject eye, such as an induction generator, may be configured to create a stimulus, such as a magnetic field, for an implanted ring that, when stimulated, may change the curvature, and thus the dioptric power, of the eye, thereby approximating natural accommodation.

For example, in response to a created magnetic field, a ring implanted on or in the cornea or limbus and magnetically coupled to the induction generator may be configured to constrict in response to the created magnetic field. This corneal constriction may serve to increase the refractive power of the cornea. The constriction of the cornea may be caused by a bending of the ring.

The ring may comprise, for example, an ionic-polymeric material having properties causing it to bend in response to a voltage being applied to the material. Thus, the stimulus, such as the induction generator, may be located proximate to or remote from the implanted ring. For example, the induction generation may be implanted underneath the skin. Optionally, the ring may be encapsulated by a silicon shell, as well as coated with a collagen film, which may serve as an additional mechanism to adhere the ring via implantation at the surface of the cornea.

Accordingly, embodiments of the present disclosure may be used to restore accommodation, or, in effect, compensate for a lack of accommodation of the crystalline lens or implanted IOL in case of pseudophakia, using an implantable ring in the cornea or limbus that is controlled by a stimulus outside the cornea. Specifically, the ring may be able to contract or relax in a controlled way in order to affect the curvature of the cornea. By changing the curvature, the ring may also change the dioptric power of the cornea, and therefore also the dioptric power of the eye.

BRIEF DESCRIPTION OF THE FIGURES

Understanding of the present invention will be facilitated by consideration of the following detailed description of the preferred embodiments of the present invention taken in conjunction with the accompanying drawings, in which like numerals refer to like parts:

FIG. 5(b) illustrates an example of an implanted ring in an activated state according to embodiments of the present invention.

DETAILED DESCRIPTION OF THE PREFERRED EMBODIMENTS

It is to be understood that the figures and descriptions of the present invention have been simplified to illustrate elements that are relevant for a clear understanding of the present invention, while eliminating, for the purpose of clarity, many other elements found in typical intraocular devices. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Embodiments of the present disclosure include an apparatus, system and method for constricting a cornea of a human eye. A control device external to the subject eye may be configured to create a stimulus, such as a magnetic field, for an implanted ring that, when stimulated, may change the curvature, and thus the dioptric power, of the eye, thereby approximating natural accommodation.

More particularly, embodiments may include a magnetic induction generator and an implantable band that together approximate natural accommodation, or, in effect, compensate for a lack of accommodation, of the crystalline lens or implanted IOL in case of pseudophakia. Specifically, through magnetic induction affected by the magnetic induction generator, the ring may be able to contract or relax in a controlled way in order to affect the curvature of the cornea. By changing the curvature, the ring may also change the dioptric power of the cornea, and therefore, also the dioptric power of the eye.

Figure 1:
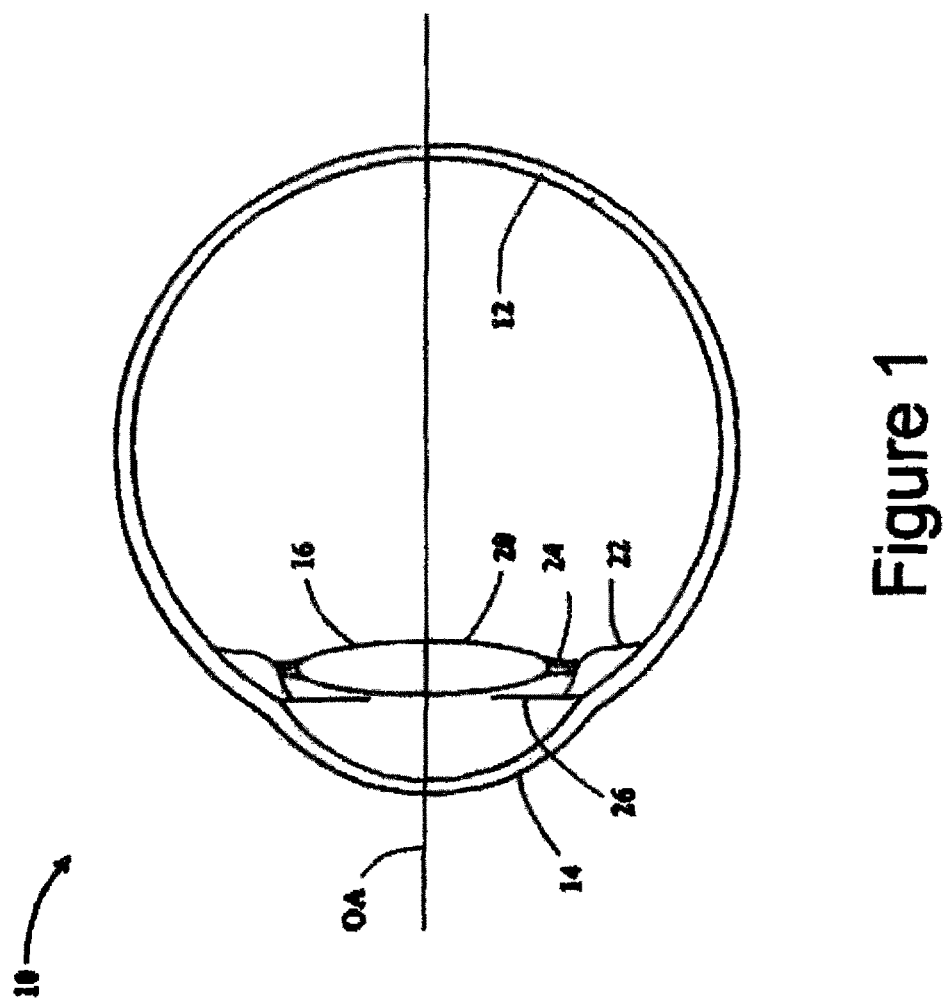
FIG. 1 illustrates a diagram of a human eye.

FIG. 1 is a diagram of an eye. Eye 10 includes retina 12 for receiving an image produced by cornea 14 and natural lens 16 from light incident upon eye 10. Natural lens 16 is disposed within capsular bag 20, which separates anterior and posterior parts of eye 10. Capsular bag 20 is a resilient material that changes the shape and/or location of natural lens 16 in response to ocular forces produced when ciliary muscles 22 relax and stretch natural lens 16 via zonules 24 disposed about an equatorial region of capsular bag 20.

This shape change effectuated by ciliary muscles 22 may flatten natural lens 16, thereby producing a relatively low optical power for providing distant vision in an emmetropic eye. To produce intermediate and/or near vision, ciliary muscles 22 contract, thereby relieving tension on zonules 24. The resiliency of capsular bag 20 thus provides an ocular force to modify the curvature of natural lens 16, to thereby provide an optical power suitable for required vision. This modification, or accommodation, allows for changes of the focus of the eye for different viewing distances.

An eye affected by presbyopia often loses the ability to rapidly and easily refocus on objects at varying distances. The ability to focus on objects at near distances may also be lost. Although the condition progresses over the lifetime of an individual, the effects of presbyopia usually become noticeable after the age of 45 years. For example, the crystalline lens may lose a substantial amount of its elastic properties and may have a limited ability to change shape.

To, in effect, compensate for the loss of elastic properties of the crystalline lens, embodiments of the present disclosure include an implantable ring that may contract or relax in a controlled way in order to affect the curvature of the cornea. As such, embodiments may serve to counteract the effects of presbyopia enabling an affected eye to again be able to change focus for objects at varying distances.

Figure 2:
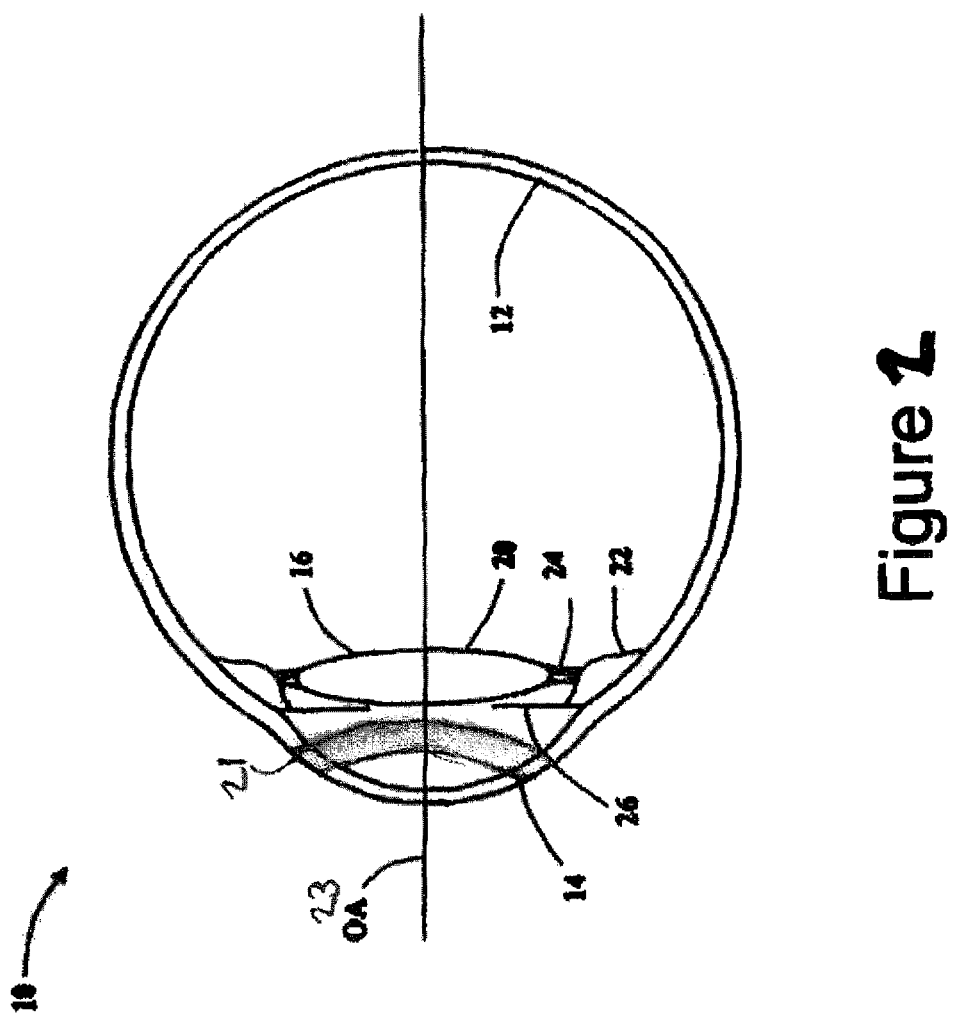
FIG. 2 illustrates an example of a ring affixed to the eye according to embodiments of the present disclosure.

FIG. 2 illustrates the ring 21 implanted in the eye 10 according to embodiments of the present disclosure. The ring 21 may be surgically implanted, such as by suturing, into the anterior surface of the cornea 14, and may preferably be centered around an optical axis 23 through the center of the cornea 14. Alternatively, analogous to the insertion of corneal onlays, the ring 21 may be implanted under a thin outer layer of cells of the cornea 14 otherwise known as the epithelium (not shown). More specifically, an instrument may be used to create a pocket between the epithelium and the stroma, and the ring may be implanted in this space. As a further alternative, the ring may be implanted in the corneal limbus (not shown), located at the border of the cornea and the sclera.

Figure 3:
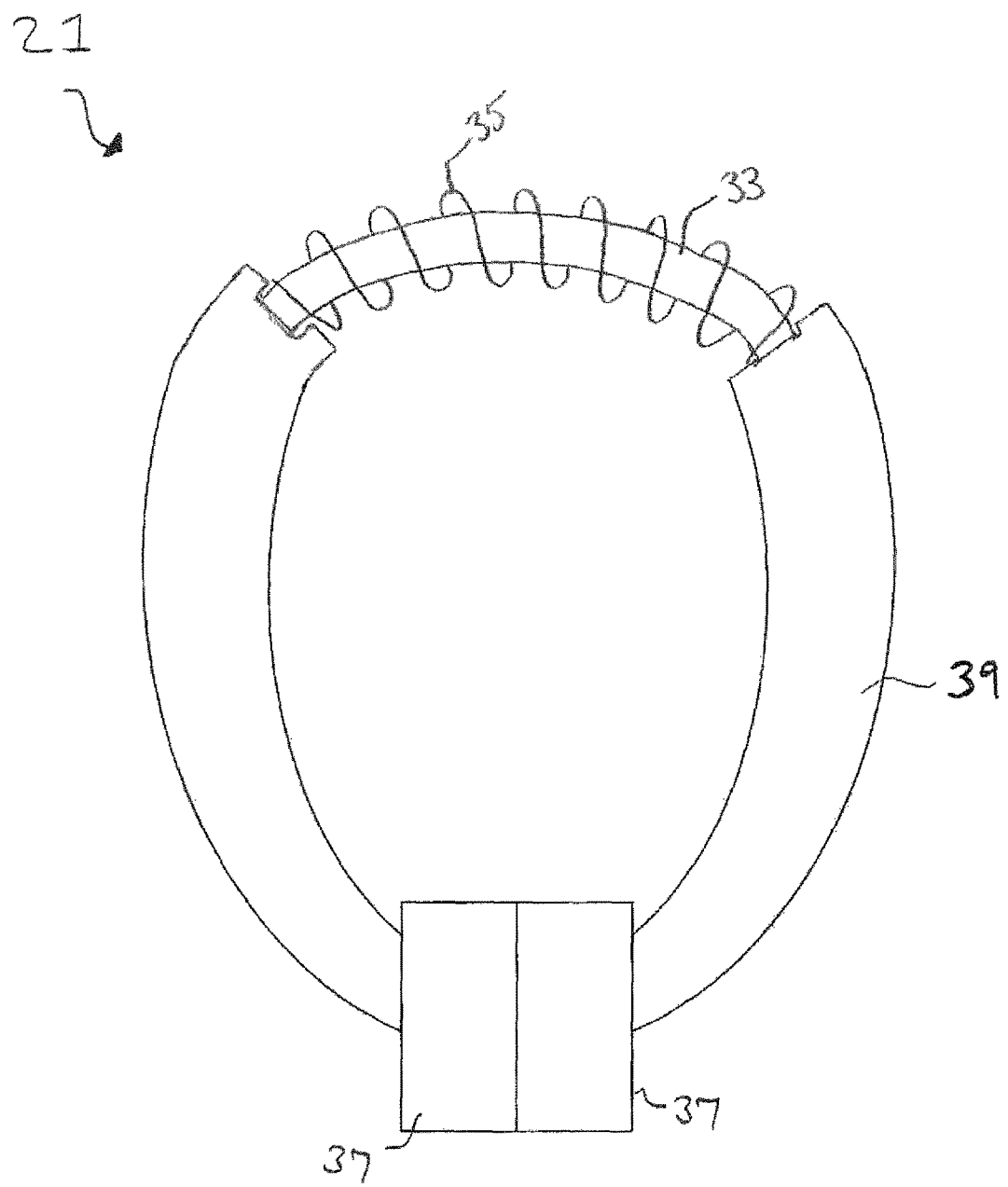
FIG. 3 illustrates an exploded view of an implantable ring according to embodiments of the present disclosure.

FIG. 3 shows an exploded view of implantable ring 21 according to embodiments of the present disclosure. In this exemplary embodiment, the implantable ring 21 includes a receiver for a stimulus from a stimulator, i.e., from a control device, that effects a constriction of the ring 21. In the exemplary illustration, the ring 21 may comprise an embedded band 33 of ionic polymer-metal composite (IPMC) material which is suitable to act as an artificial muscle, that is, which constricts and relaxes, under an applied and removed voltage, respectively. The IPMC band 33 may be composed of an ionic polymer like Nafion or Flemion, although any ionic polymer material exhibiting artificial muscle behavior may be employed.

To create the applied voltage to control the IPMC band 33, magnetic induction coils 35 (composed of any conducting material as known in the art, e.g., copper) may be wrapped around the band's planar surface. The implantable ring 21 (including the IPMC band and coils 35) may be enclosed by connectable ends 37, and the entirety of the ring 21 and the connectable ends 37 may be enclosed by a silicon shell 39. The connectable ends 37 may snap or bond together by any known means, such as sutures, magnets, bio-compatible adhesive, velcro, or the like.

Optionally, so as to aid in adhesion to the implanted location with respect to the cornea 14, the implantable ring 21 may also be coated with a thin bio-compatible adhesive. For example, the ring may be coated in a thin collagen film (not shown), which may be composed of gelatin, a glycosaminoglycan such as chondroitan sulfate, and carboxymethyl cellulose.

The operation of the implantable ring 21 is such that, when the external voltage is applied to the IPMC band 33, cations inside its membrane carry solvent molecules toward the cathode, and the movement creates bending, causing the entire implanted ring 21 to constrict. This constricting exerts a pressure on the cornea 14, thereby altering the cornea's curvature. This change in curvature alters the dioptric power of the cornea, and therefore, also the dioptric power of the eye.

Figure 4:
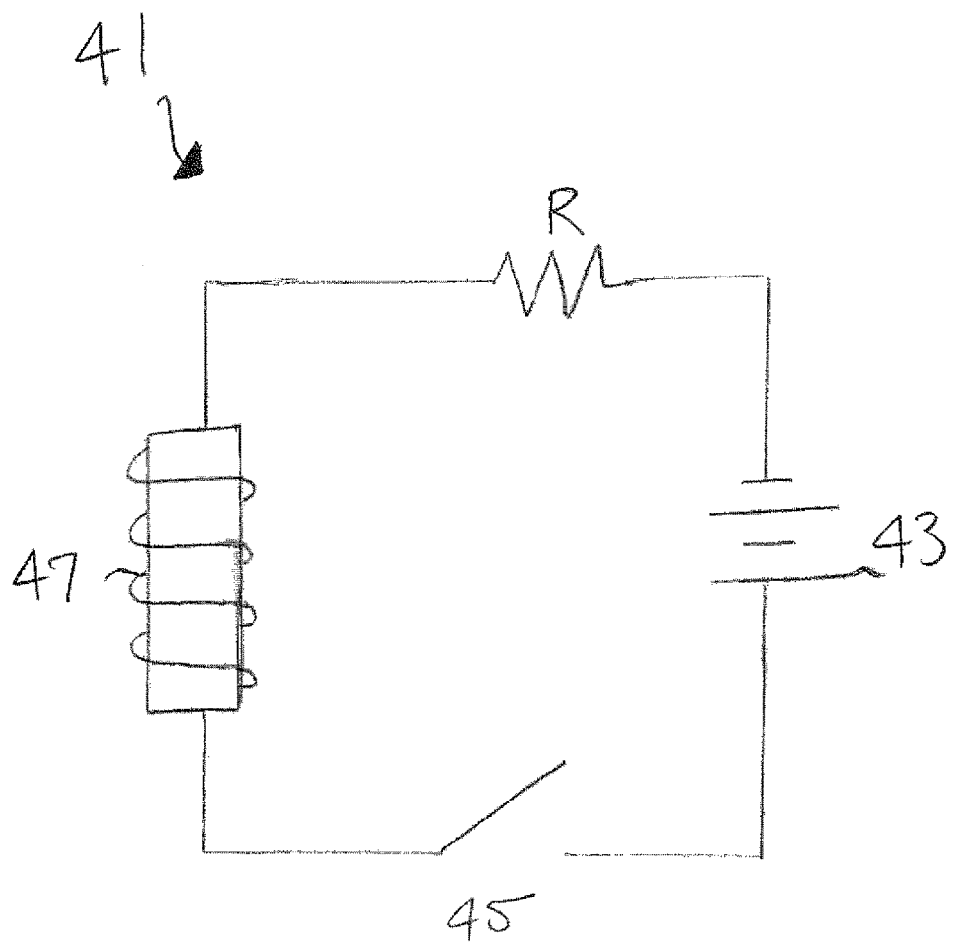
FIG. 4 illustrates a magnetic induction generator according to embodiments of the present disclosure.

FIG. 4 shows a magnetic induction generator 41 powered by a battery 43 employed to induce the voltage in the magnetic induction coils 35 in the associated implantable ring 21. Because the magnetic induction coils 35 are a component of the device getting its power from a the magnetic induction generator 41 (also known as a primary circuit supplying the voltage), the magnetic induction coils may be otherwise known as "secondary". More specifically, as a component switch 45 is closed, a voltage may be induced in "primary" induction coil 47, thereby generating a magnetic field. This generated magnetic field alters the magnetic environment of the associated secondary magnetic inductive coils 35, thereby inducing a voltage causing the implantable ring 21 to constrict.

Figure 5A:
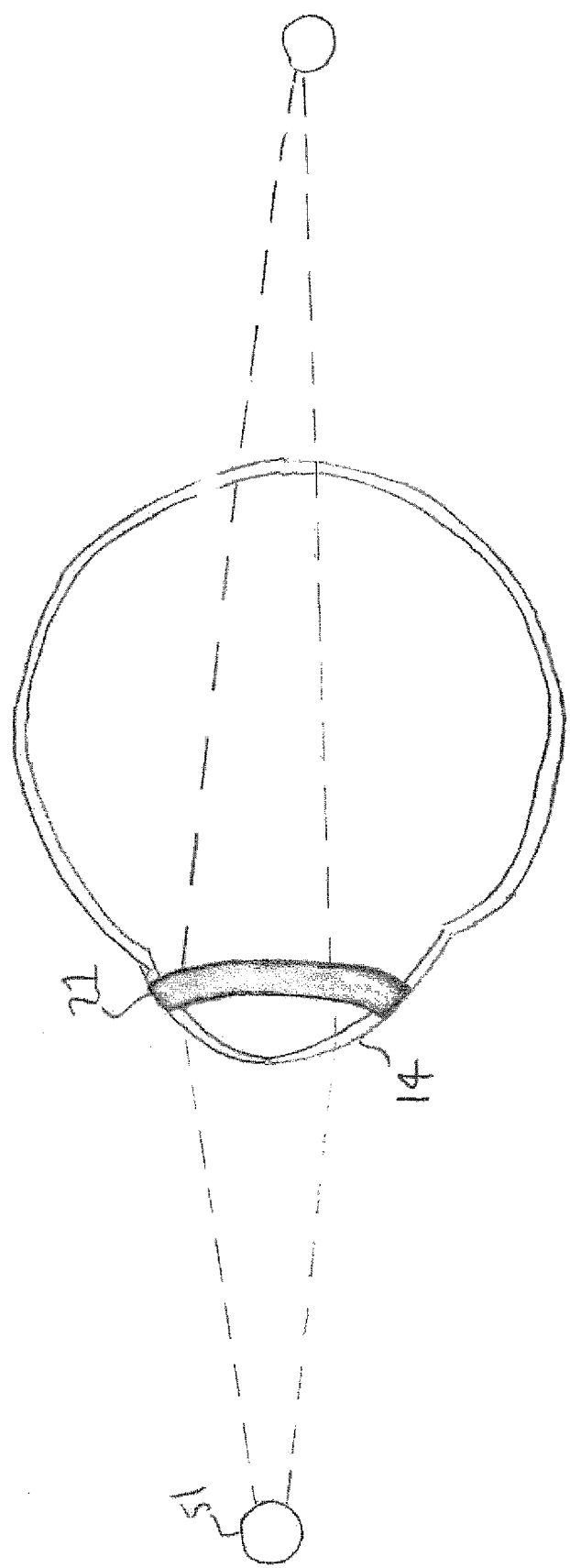
FIG. 5(a) illustrates an example of an implanted ring in a relaxed state according to embodiments of the present disclosure.

FIG. 5(a) shows the implantable ring 21 of FIG. 2 around the anterior surface of the cornea 14 of the eye in a relaxed non-induced/non-stimulated state. In operation, as shown in FIG. 5(b), under an induced voltage from the external magnetic induction generator 41, the implantable ring 21 causes the cornea to change shape resulting in an altered refractive power. This increased refractive power may serve to compensate for the lack of accommodation of the crystalline lens or implanted IOL in case of pseudophakia. Consequently, the implantable ring 21 may serve to properly coincide the retina/macula region with the focal point of the eye 10 for viewing an object 51, thus correcting, for example, for presbyopia.

The stimulator, such as the magnetic induction generator 41, may, for example, be affixed to any portion of the ear of the person wearing the implanting ring, although the location of the generator should not be so limited. For example, the generators may be located anywhere on the person's body, or article of clothing. For example, the generators may be worn as a wristband, headband, or even be configured to take the form of decorative jewelry in the form of earpieces (e.g., earrings or neckwear). Further still, the induction generator 41 may be surgically implanted under the skin in a manner and location so as the person may conveniently turn on or off the generator 41 by the touch of a finger, for example.

Further, those skilled in the art will appreciate, in light of the disclosure provided herein, that other stimulus receiver and stimulator pairs (in addition to the magnetic coupling and voltage pair discussed above) may be employed to stimulate ring 21, and that such stimulator may be remotely or locally external to the eye, and may be controlled by any known means, such as manual actuation, voice activation, muscular cues (such as squinting or ciliary muscle activation), or the like.

Of course, those skilled in the art will appreciate that, in light of the disclosed embodiments, a magnetic field may lose strength the further it is from its primary source. As such, it may be preferable for the stimulator, such as the magnetic induction generator 41, be located in a relatively close proximity to the implanted ring to ensure a sufficient stimulus, such as a sufficient voltage, is induced.

It is also important to note that the induced voltage need not remain constant. Stated differently, the induced voltage may vary or be induced by a variety of techniques. For example, any change in the magnetic environment may cause a voltage to be "induced" in the coil. No matter how the change is produced, the voltage may be generated. This change could be produced by changing the magnetic field strength, moving a magnet toward or away from the coil, moving the coil into or out of the magnetic field, rotating the coil relative to the magnet, etc.

Further still, the induced voltage may be pre-programmed to produce a certain result, which may translate into a specific dioptric power of the cornea. For example, applying a voltage of approximately 1 volt may translate to a specific change of 1 diopter. On the other hand, applying a voltage of approximately 5 volts may result in a larger increase of refractive power of the cornea, potentially on the order of 3 diopters.

In light of the above discussion, any of these aforediscussed techniques to induce a voltage (and program, to the extent possible, a particular change in refractive corneal power) may be effectuated by the implementation of a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the disclosure herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary designs, the functions (e.g., the adjustment of the induced voltage) described may be implemented in hardware, software, firmware, or any combination thereof. If implemented in software, the functions may be stored on or transmitted over as one or more instructions or code on a computer-readable medium, and preferably on a non-transitory computer-readable medium. Computer-readable media includes both computer storage media and communication media including any medium that facilitates transfer of a computer program from one place to another. A storage medium may be any available medium that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Figure 6:
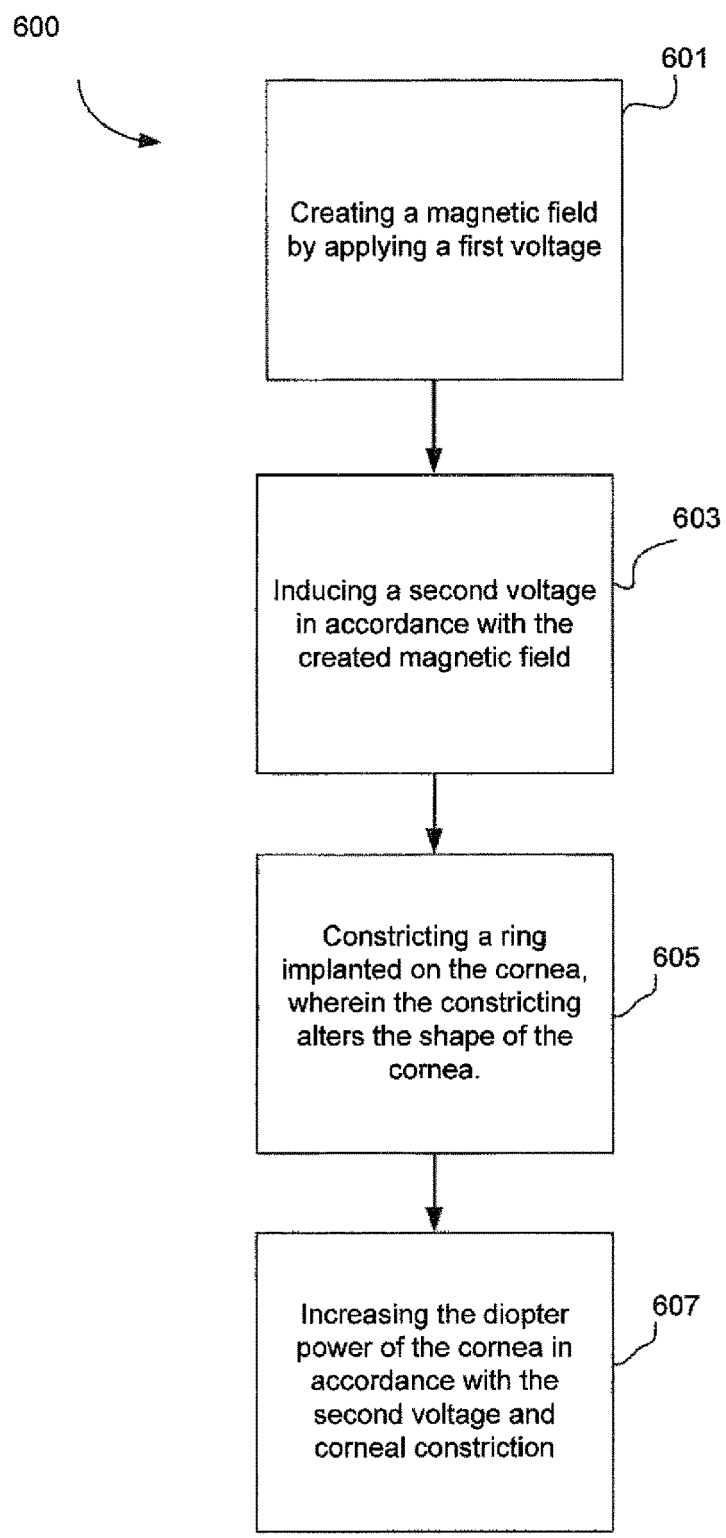
FIG. 6 illustrates a method of actively constricting a cornea of a human eye according to embodiments of the present disclosure.

FIG. 6 illustrates a method 600 for actively constricting a cornea of a human eye. The method 600 may include, at step 601, creating a stimulus, such as creating a magnetic field by applying a first voltage. Method 600 may further include receiving the stimulus at an implanted ring, such as by inducing a receiving second voltage in accordance with the created magnetic field, at step 603. In accordance with the received stimulus, step 605 may include constricting the ring implanted to the cornea, wherein the constricting alters the shape of the cornea. Step 607 may include increasing the dioptric power of the cornea in accordance with the corneal constriction.

Although the invention has been described and pictured in an exemplary form with a certain degree of particularity, it is understood that the present disclosure of the exemplary form has been made by way of example, and that numerous changes in the details of construction and combination and arrangement of parts and steps may be made without departing from the spirit and scope of the invention as set forth in the claims hereinafter.

The invention claimed is:

1. A method for actively constricting a cornea of a human eye, the method comprising: receiving a stimulus from external to the human eye; and inducing a constriction in a ring implanted on or in the cornea, wherein the constriction alters the shape of the cornea in accordance with the received stimulus, the ring able to contract or relax in a controlled way in order to affect curvature of the cornea, the stimulus comprises a magnetic field generated by an induction generator, and the inducing comprises a magnetic coupling to the magnetic field; whereby changing curvature of the cornea, the ring changes dioptric power of the cornea and dioptric power of the eye.

2. The method of claim 1, further comprising increasing the dioptric power in accordance with the induced constriction.

3. The method of claim 1, wherein the received stimulus comprises a predefined voltage.

4. The method of claim 1, wherein the ring comprises an ionic polymeric material.

5. The method of claim 1, wherein the stimulus is remote from the ring.

6. The method of claim 1, wherein the ring comprises a silicon shell.

7. The method of claim 1, wherein the ring is coated with a collagen film.

\* \* \* \* \*